US010668295B2

(12) United States Patent
Langer et al.

(10) Patent No.: US 10,668,295 B2
(45) Date of Patent: Jun. 2, 2020

(54) ENERGY HARVESTING STIMULATOR

(71) Applicant: MR3 MEDICAL, LLC, North Oaks, MN (US)

(72) Inventors: Alois Langer, Pasadena, MD (US); Morton M. Mower, Denver, CO (US)

(73) Assignee: MR3 MEDICAL, LLC, North Oaks, MN (US)

( * ) Notice: Subject to any disclaimer, the term of this patent is extended or adjusted under 35 U.S.C. 154(b) by 201 days.

(21) Appl. No.: 14/695,225

(22) Filed: Apr. 24, 2015

(65) Prior Publication Data

US 2015/0306403 A1    Oct. 29, 2015

Related U.S. Application Data

(60) Provisional application No. 61/984,542, filed on Apr. 25, 2014.

(51) Int. Cl.
*A61N 1/378* (2006.01)
*A61N 1/36* (2006.01)

(52) U.S. Cl.
CPC ....... *A61N 1/3787* (2013.01); *A61N 1/36014* (2013.01)

(58) Field of Classification Search
CPC .......................... A61N 1/36014; A61N 1/3787
See application file for complete search history.

(56) References Cited

U.S. PATENT DOCUMENTS

| 5,733,313 A * | 3/1998 | Barreras, Sr. ............ A61N 1/08 128/903 |
|---|---|---|
| 6,166,518 A * | 12/2000 | Echarri ................ A61N 1/3708 320/106 |
| 2002/0055763 A1* | 5/2002 | Zarinetchi ............ A61N 1/3787 607/61 |
| 2010/0171394 A1* | 7/2010 | Glenn .................... A61N 1/372 310/339 |
| 2012/0143287 A1* | 6/2012 | Shodo ................ A61N 1/36046 607/72 |

* cited by examiner

*Primary Examiner* — Lindsey G Wehrheim
(74) *Attorney, Agent, or Firm* — Oblon, McClelland, Maier & Neustadt, L.L.P.

(57) ABSTRACT

A stimulation device that stimulates living tissue includes an energy harvesting circuit that receives an output signal from another device and that powers the stimulation device, immediately or otherwise, using the output signal. The stimulation devices also includes a stimulation circuit that generates a stimulation signal to elicit a predetermined response from the living tissue, and at least one lead that delivers the stimulation signal to the living tissue.

19 Claims, 7 Drawing Sheets

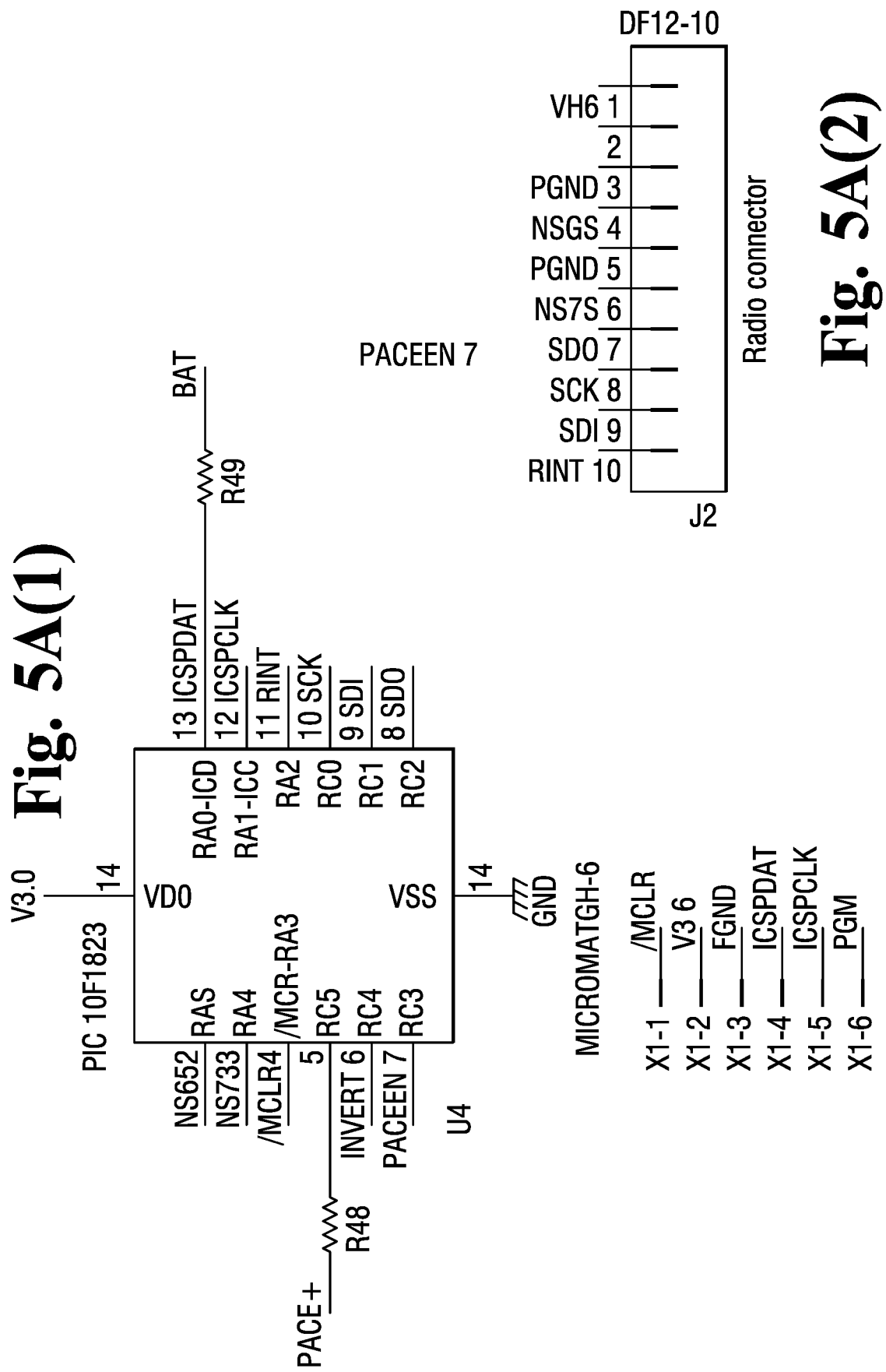

ENERGY HARVESTING STIMULATOR

CROSS-REFERENCE TO RELATED APPLICATIONS

This non-provisional application claims the benefit of priority to provisional U.S. Application No. 61/984,542 entitled "Electrical Stimulator Powered by Harvested Energy" and filed on Apr. 25, 2014. The entire contents of provisional U.S. Application No. 61/984,542 are incorporated herein by reference.

FIELD

The present disclosure is directed to stimulation devices that electrically stimulate living tissue, and in particular to stimulation devices that electrically stimulate living tissue without a dedicated power supply.

BACKGROUND

Conventional stimulation devices that stimulate living tissue, such as organs and cells of a human body, include a battery as a source of power. In the case of the heart, for example, cardiac rhythm management is accomplished by the use of pacemakers and defibrillators (collectively known as cardiac stimulation devices). These devices typically deliver pulses to the heart in order to cause the heart to contract in a manner according to the programming of the cardiac stimulation device.

Whether a cardiac stimulation device or some other stimulation device, manufacturers of these conventional devices must guarantee the reliability and resistance to battery leakage of these devices. This means that new stimulation devices must undergo extremely stringent testing, which adds to the expense of development and testing.

SUMMARY

In view of the above, a need exists for stimulation devices that are able to stimulate living tissue, such as the heart, but that do not include a dedicated power source, such as batteries, in order to avoid the added costs of certifying the device's resistance to battery leakage.

The stimulation pulses produced by a conventional stimulation device, which includes a battery, may be viewed as a source of energy that may be harvested for use by another, auxiliary device (also referred to herein as an "energy harvesting stimulator" or an energy harvesting stimulation device"). The final output pulses of the energy harvesting stimulator can have amplitudes, polarities and combinations that differ from the pulses of the conventional stimulation device from which energy is harvested. The energy harvesting device may be implantable or may remain external to the body. A major improvement for both implantable and non-implantable devices is the ability to make changes to the waveforms in the energy harvesting stimulator that is added to the conventional stimulation device. Also, in addition to using the harvested energy to alter the output characteristics of each stimulatory pulse, the energy harvesting stimulator may store some energy to power other types of functions that may be used intermittently, such as radio-telemetry, programming of the energy harvesting stimulator, and/or running a microprocessor.

In view of the above discussion, one exemplary aspect of the present disclosure is a stimulation device that stimulates living tissue, and includes an energy harvesting circuit that receives an output signal from another device and that powers the stimulation device, immediately or otherwise, using the output signal. The stimulation devices also includes a stimulation circuit that generates a stimulation signal to elicit a predetermined response from the living tissue, and at least one lead that delivers the stimulation signal to the living tissue.

BRIEF DESCRIPTION OF THE DRAWINGS

A more complete appreciation of the present disclosure and many of the attendant advantages thereof will be readily obtained as the same becomes better understood by reference to the following detailed description when considered in connection with the accompanying drawings, wherein.

DETAILED DESCRIPTION

Figure 1:
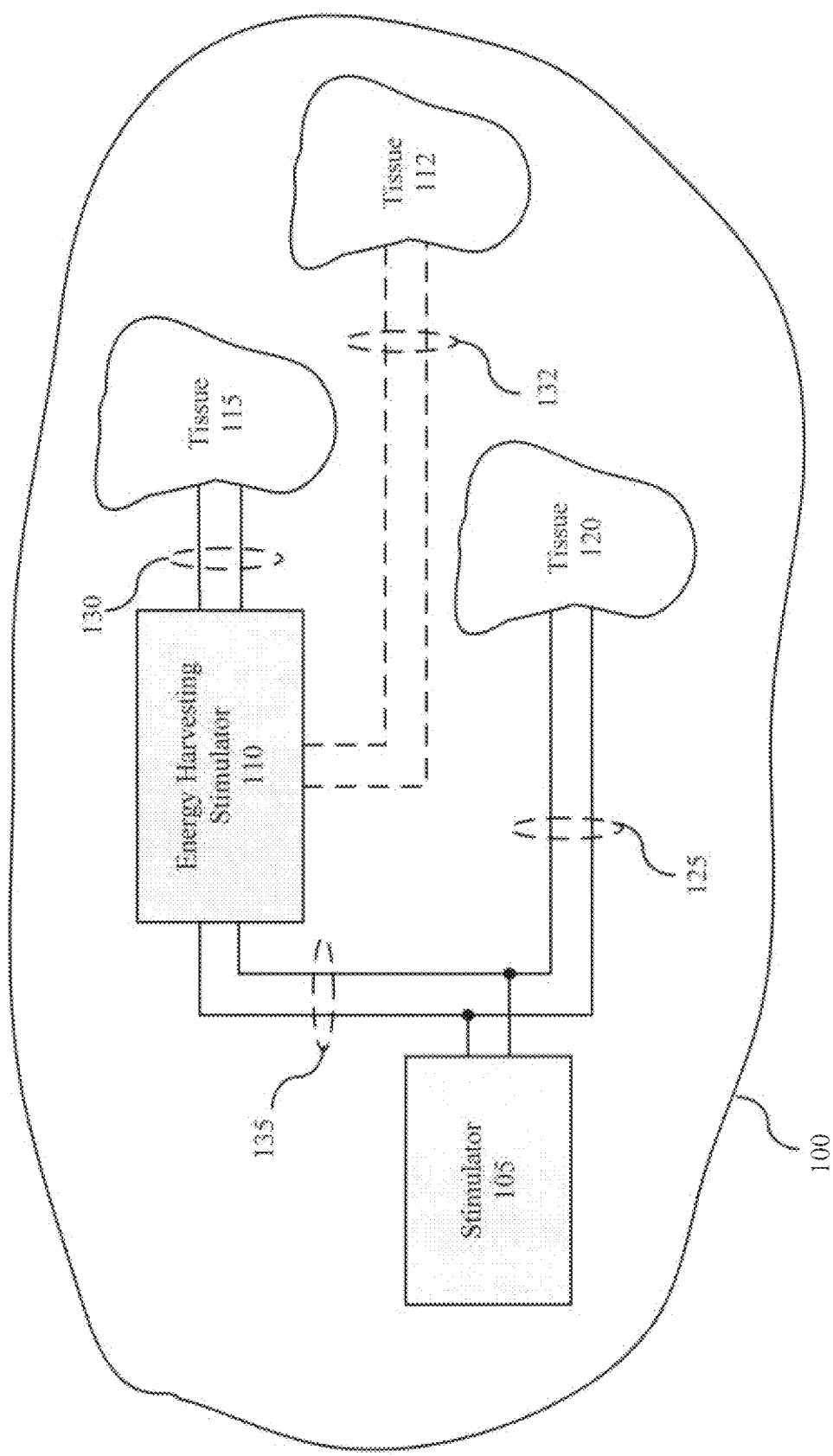
FIG. 1 is a diagram of a living body with an energy harvesting stimulation device according to exemplary aspects of the present disclosure.

Referring now to the drawings, wherein like reference numerals designate identical or corresponding parts throughout the several views, FIG. 1 is a diagram of a living body 100 that includes an energy harvesting stimulator 110 according to exemplary aspects of the present disclosure. In FIG. 1, the energy harvesting stimulator stimulates living tissue 115 via a pair of leads 130. The stimulation signal provided by the energy harvesting stimulator 110 to the living tissue 115 may be of any waveform known in the art. For example, the stimulation signal may include bi-phasic pulses, mono-phasic pulses, poly-phasic pulses or any combination thereof. The stimulation signal may also provide anodal and/or cathodal stimulation to the living tissue 115. Thus, the exact waveform of the stimulation signal is not limiting upon this disclosure, and any waveform may be used as long as it elicits the desired response from the living tissue 115.

To power itself, the energy harvesting stimulator 110 includes a pair of power leads 135 that connect to the output leads 125 of another device, such as stimulator 105. The stimulator 105 may, for example, be a conventional pacemaker that includes batteries as a dedicated power source. When the stimulator 105 generates an output signal and provides that output signal to living tissue 120 via output leads 125, the power leads 135 of the energy harvesting stimulator 110 divert a portion of the energy of the output signal. This diverted energy is then used by the energy harvesting stimulator 110 to power its circuits and to generate the stimulation signal provided to the living tissue 115 via the leads 130. Thus, the energy harvesting device 110 does not need a dedicated battery power source, and instead relies on the energy diverted from the output signal of the stimulator 105.

Of course, the output signal of the stimulator 105 may be provided to living tissue 120 via leads 125 in order to elicit a predetermined response from that tissue 120. In other words, the output signal of the stimulator 105 is used to stimulate the living tissue 120. As explained in greater detail below, the energy harvesting stimulator 110 includes a power circuit that limits the amount of energy diverted from the stimulation signal of the stimulator 105 so that the output signal can properly stimulate the tissue 120 after a portion of the energy is diverted. The stimulator 105 may require adjustment via radio-telemetry in order to accommodate the additional load from the energy harvesting stimulator 110, or may be able to accommodate the additional load without adjustment. In either case, no special modifications to the stimulator are required, and the energy harvesting stimulator 110 may simply be attached to a stimulator already in service in the living body 100. In some cases the output leads 125 of stimulator 105 are not connected to living tissue but rather only to the harvesting stimulator which then alone stimulates the appropriate tissue 115.

Though the energy harvesting stimulator 110 draws power from the output signal of the stimulator 105, the stimulation signal of the energy harvesting stimulator 110 is independent of the output signal of the stimulator 105. For example, if the stimulator 105 is a pacemaker that uses mono-phasic pulse stimulation, the energy harvesting stimulator 110 may be a bi-phasic stimulator that uses bi-phasic pulse stimulation. In such a case, the tissues 115 and 120 may both be cardiac tissues. However, the tissues 115 and 120 may also be unrelated tissues. For example tissue 115 may be cardiac tissue while tissue 120 may be nerve tissue unrelated to the heart. This is possible because the energy harvesting stimulator 110 uses the output of the stimulator 105 only for power. Thus, even in the case where the energy harvesting stimulator 110 does not store any power and generates the stimulation signal immediately upon receipt of the output signal of the stimulator 105, the output signal of the stimulator 110 and the stimulation signal of the energy harvesting stimulator 110 remain independent.

As also illustrated in FIG. 1, the energy harvesting stimulator may also be provided with an additional set of leads 132 to stimulate another tissue 112. As can be appreciated, the other tissue 112 may be related to one or both of tissues 115 or 120 or may be completely unrelated to these tissues. Likewise the stimulating signal provided by the energy harvesting stimulator 110 via the leads 132 may be derived from the stimulating signal provided through leads 130, or may be independent of the signal through the leads 130. Of course, one of ordinary skill would recognize that the stimulating signal provided via leads 132 may include bi-phasic pulses, mono-phasic pulses, poly-phasic pulses or any combination thereof. In this way, the energy harvesting stimulator 110 may stimulate more than just one tissue. Though FIG. 1 illustrates the energy harvesting stimulator 110 stimulates one or two tissues, the energy harvesting stimulator 110 may stimulate any number of tissues without departing from the scope of the present disclosure.

In FIG. 1 the energy harvesting stimulator 110 and the stimulator 105 are illustrated as implanted in the living body 100 since these devices may be implantable. However, one or both of devices may be situated outside the living body 100, as would be appreciated by one of ordinary skill in the art. Moreover, the living body 100 may be a human body or an animal body, and therefore the tissues 115 and 120 may be human tissue or animal tissue, without departing from the scope of the present disclosure.

Figure 2A:
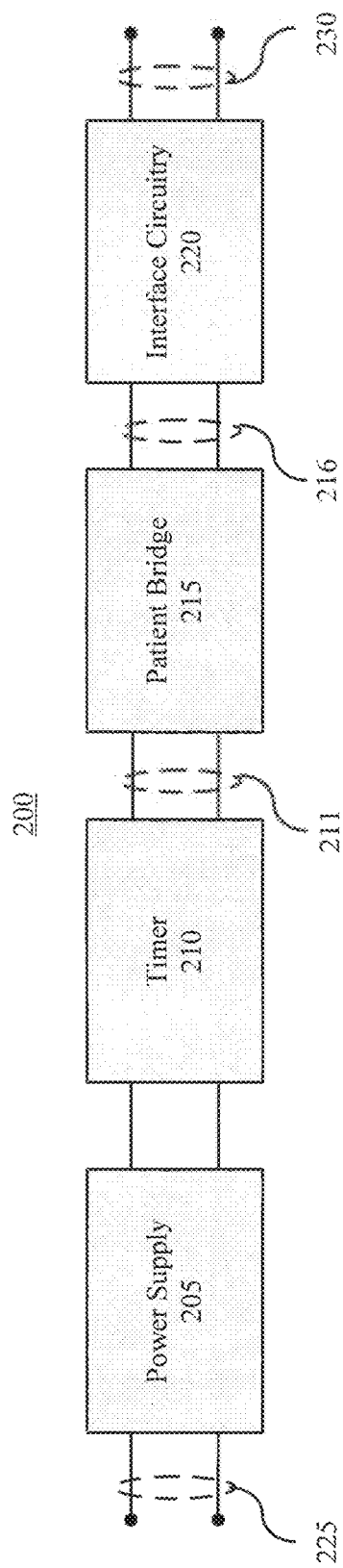
FIG. 2A is a functional diagram of an energy harvesting stimulation device according to exemplary aspects of the present disclosure.

FIG. 2A is a block diagram of an energy harvesting stimulator 200 that may be used as the energy harvesting stimulator 110 of FIG. 1. This particular example of an energy harvesting stimulator changes the mono-phasic cathodal pulse from an implanted pacemaker to a bi-phasic stimulation pulse. In FIG. 2A, the energy harvesting stimulator 200 includes a power supply circuit 205 that receives the output signal of, for example, stimulator 105 via the leads 225. The power supply circuit 205 may simply be a connector, but preferably offers some level of current regulation in order to limit the amount of energy drawn by the energy harvesting stimulator 200 so as not to interfere with the stimulation provided by the stimulator 105.

Figure 2C:
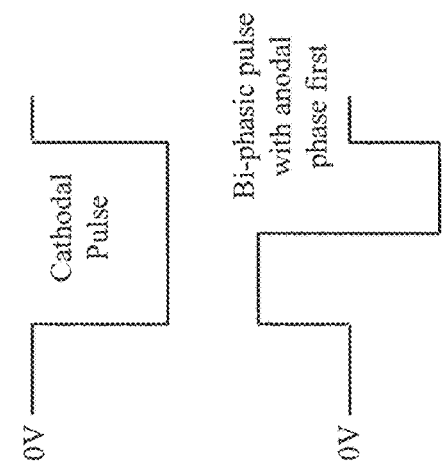
FIG. 2C is a diagram of pulses generated by the patient bridge of FIG. 2B according to exemplary embodiments of the present disclosure.
Figure 2B:
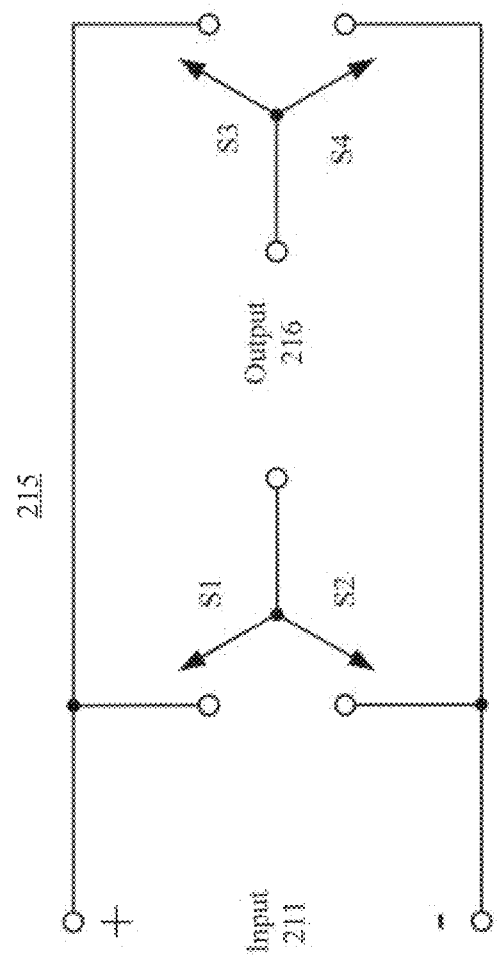
FIG. 2B is a conceptual drawing of a patient bridge according to exemplary aspects of the present disclosure.

The energy harvesting stimulator 200 of FIG. 2A does not store energy diverted from the output signal of the stimulator 105. Instead, the power supply circuit 205 provides the energy to a timer circuit 210 which determines a pulse width of the pulses that form the stimulation signal of the energy harvesting stimulator 200. The output of the timer circuit 210 is provided to a patient bridge circuit, which is responsible for inverting the polarity of the stimulation signal applied to the patient and is the interface between the timer circuitry of the energy harvesting stimulator 200 and the circuitry connected to the living tissue 115. A conceptual version of the patient bridge is shown in FIG. 2B and is sometimes referred to as an H bridge. It consists of 4 switches, S1-S4. In one state S1 and S4 are closed while S2 and S3 are open presenting one polarity to patient output 216. In the other state, S2 and S3 are closed while S1 and S4 are open presenting the opposite polarity to the output. The switches are controlled by the timer thus inverting the polarity after the timer times out. The output of the patient bridge 215 is then provided to interface circuitry 220 that generates the stimulation signal as a bi-phasic pulse having a first phase pulse width based on the output 211 of the timer circuit 210 as illustrated in FIG. 2C. The stimulation signal is then provided to living tissue 115 in order to elicit a predetermined response, such as muscle contraction for example. Though in FIG. 2A the power supply circuit 205, the timer circuit 210, the patient bridge 215 and the pulse generator 220 are illustrated as separate circuit blocks, the functionality of these blocks can be combined in order to reduce the number of circuits as would be recognized by one of ordinary skill in the art.

Figure 3:
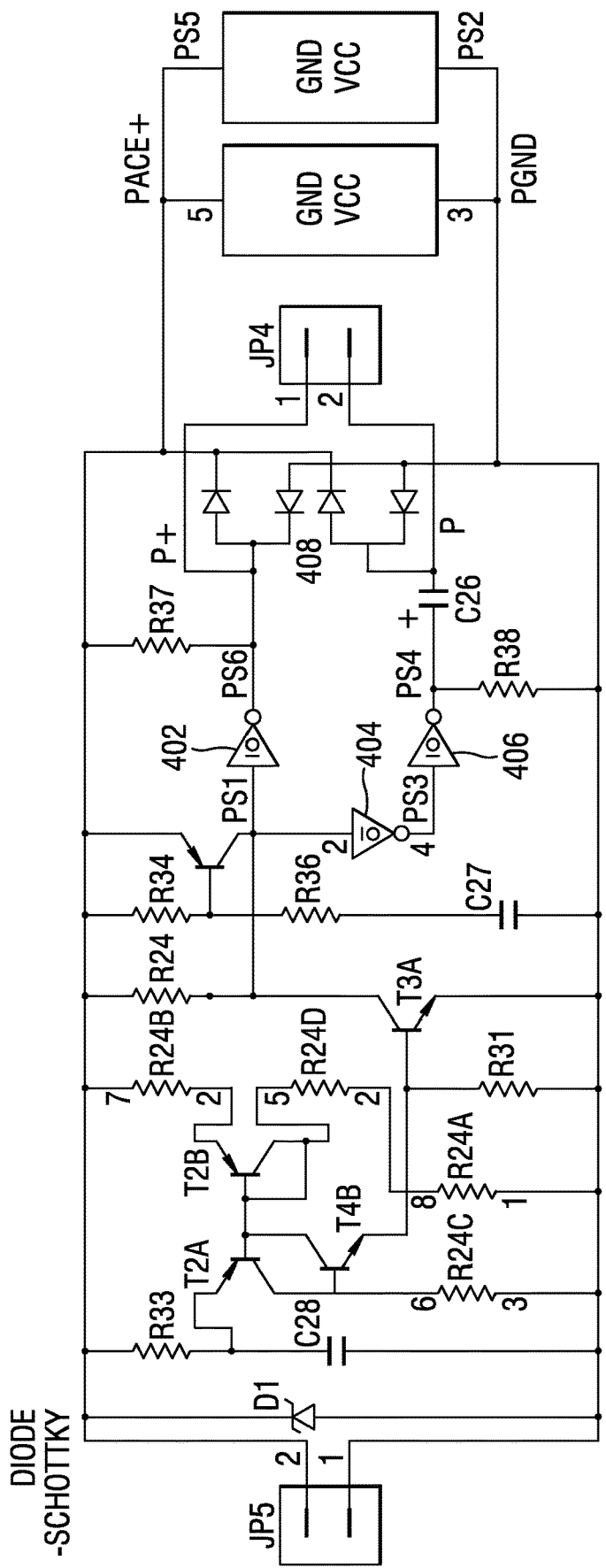
FIG. 3 is a circuit diagram of an energy harvesting stimulation device according to exemplary aspects of the present disclosure.

Next, FIG. 3 is a more detailed circuit diagram of this exemplary energy harvesting stimulator that does not store energy harvested from the output leads of another stimulator, such as stimulator 105 of FIG. 1. In FIG. 3, the energy harvesting stimulator is connected to the leads of the other stimulator 105 via the connector JP5. The transistors T2A, T2B, T3A, T3B, T4B and their associated passive components form the timer circuit 210 of FIG. 2, and inverters 402, 404 and 406 form the patient bridge 215. Inverters have push pull output transistors analogous to the switches in FIG. 2A, each inverter providing one-half of the "H". The diodes 408 are a protection circuit that protects the inverters from voltage and/or current spikes such as those that result from application of a defibrillator. The stimulation signal generated by the inverters 402, 404 and 406, also passing through the interface circuitry R37, R38, and C26, is provided to the living tissue via the connector JP4. As can be seen in FIG.

3, the connector JP5 is connected to the traces that form the positive and negative power supply rails of the energy harvesting stimulator to power the circuitry such as the timer and inverters 402, 404 and 406. Since all the power is provided by the input pulse, this implements the energy harvesting function.

The energy harvesting stimulator of FIG. 3 may be implemented as discrete components. For example, the transistors, resistors, capacitors, diodes and inverters may be discrete components that are placed on a printed circuit board with copper traces to make the interconnections among the components. The energy harvesting stimulator may also be implemented as a single chip, for example as an application specific integrated circuit (ASIC), or as a combination of an ASIC and discrete componentry. Numerous other implementations of the energy harvesting stimulator's circuitry are also possible without departing from the scope of the present disclosure.

Figure 4:
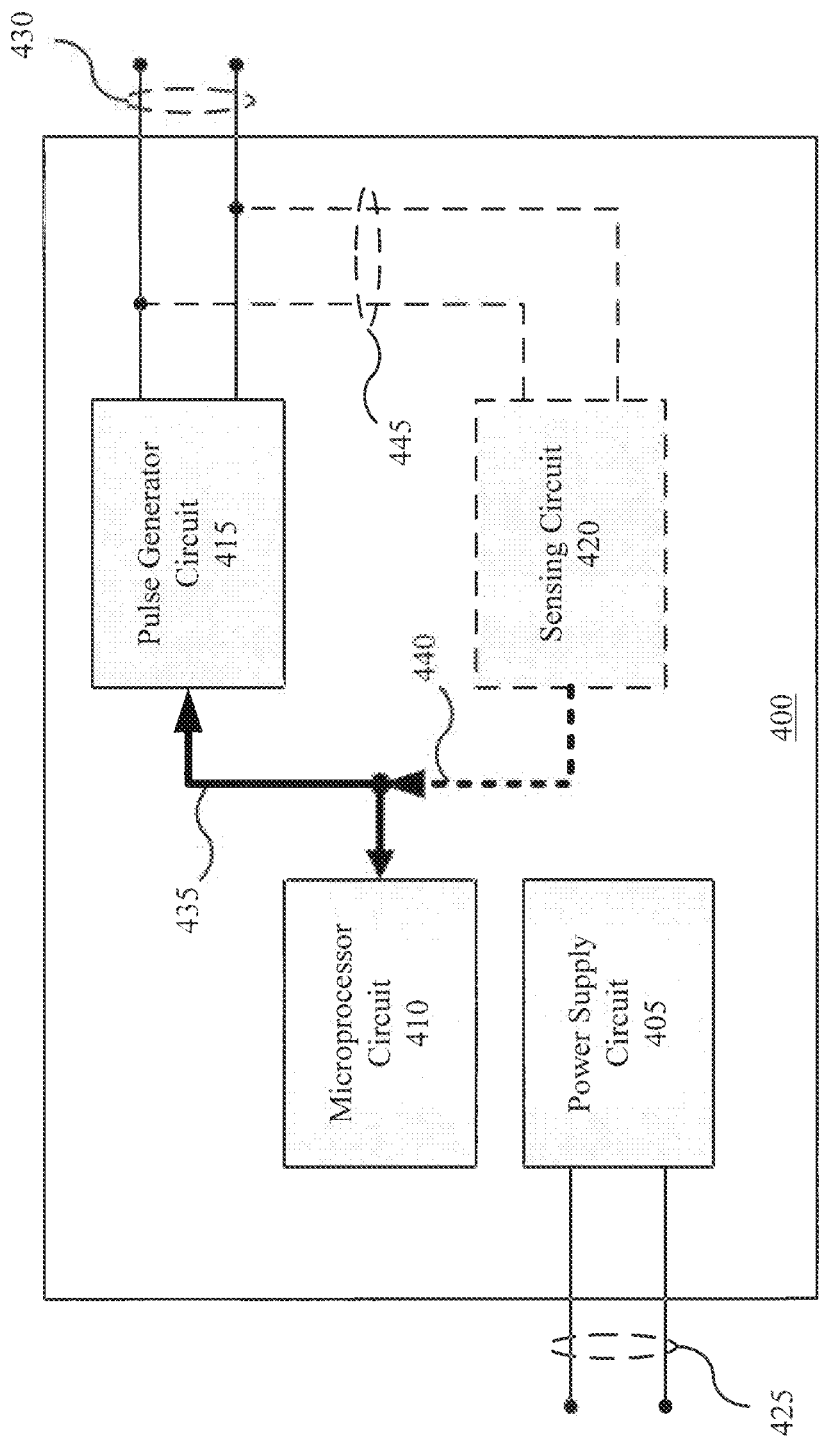
FIG. 4 is a diagram of another energy harvesting stimulation device according to exemplary embodiments of the present disclosure.

Next, FIG. 4 is a block diagram of an energy harvesting stimulator 400 that stores energy in accordance with exemplary aspects of the present disclosure. In FIG. 4, the leads 425 that attach to another stimulator, such as stimulator 105 of FIG. 1, are connected to a power supply circuit 405. This power supply circuit 405 may include an energy device, such as a capacitor (not shown) to store the energy diverted from as the output signal of the stimulator 105. The power supply circuit 405 also includes a current regulator circuit to limit the amount of energy diverted from the output signal of the stimulator 105 even when the capacitor is fully discharged. This assures that the output signal of the stimulator 105 conserves sufficient energy to adequately stimulate living tissue 120 as originally intended by the stimulator 105.

The power supply circuit 205 of FIG. 4 may also include a voltage regulator, such as a switching voltage regulator to generate a stable dc voltage to power the other circuits of the energy harvesting stimulator 400 as will be explained below in greater detail. The voltage regulator may also be a linear regulator, and may be implemented using discrete components or using off-the-shelf integrated circuits, as can be appreciated.

The dc voltage output by the voltage regulator of the power supply circuit may be used to power a microprocessor 410 to perform the various functions of the energy harvesting stimulator 400. For example, the microprocessor 410 may execute computer-readable instructions in order to determine the parameters of the stimulation signal, such as pulse width, amplitude, frequency, phase, etc. The microprocessor 410 may also monitor the amount of remaining energy stored in the capacitor of the power supply circuit 405 and shutdown circuits of the energy harvesting stimulator 400 to conserve energy.

In one exemplary embodiment, the microprocessor 410 may operate in two modes. In the first mode, the microprocessor 410 may enter a low power sleep or shut down mode and may cause other circuits of the energy harvesting stimulator 400 to do the same. In this first mode, the power supply circuit 405 remains active, but because the other circuits are shut down, the power supply circuit 405 may be able to increase its store of energy diverted from the output signal of the stimulator 105.

In the second mode, the microprocessor 410 is fully active in order to perform such tasks as controlling the pulse generator circuit 415 to generate the stimulation signal. Dependent upon the application, the second mode of operation of the microprocessor 410 may slowly deplete the energy stored in the power supply circuit 405 and therefore the microprocessor 410 may only be in the second mode for a limited time. Alternatively, the microprocessor 410 may be able to function in the second mode indefinitely without depleting the energy stored in the power supply circuit 405 at a faster rate than the power supply circuit 405 is able to replenish it. In either case, the microprocessor 410 may include a timer to generate an interrupt that causes the microprocessor 410 to transition from one mode to the other at preset intervals.

Returning to FIG. 4, the microprocessor 410 is connected to a pulse generator circuit 415 via communication bus 435. As can be appreciated, the communication bus may include any number of conductors in order to implement a variety of custom and structured buses. The microprocessor 410 provides the pulse generator circuit 415 with the parameters for generating the stimulation signal via this bus 435, and the pulse generator circuit 415 generates the stimulation signal accordingly. As the pulse generator circuit 415 is substantially the same as the pulse generator circuit 220 described above with reference to FIGS. 2-3, further description is omitted for brevity.

The energy harvesting stimulator 400 may also include a sensing circuit 420 to monitor predetermined parameters of the tissue 115. For example, an electrocardiograph (ECG) waveform may be monitored, or depolarization of a cell or a group of cells may be monitored, or the heart beat rate (i.e., pulse rate) may also be monitored. Any other physiological parameter may also be monitored without departing from the scope of the present disclosure.

The sensing circuit 420 may cause the microprocessor 410 to transition from the first mode to the second mode and vice versa based on the monitored parameter. For example, if the sensing circuit monitors an ECG, the microprocessor 410 may remain in the first mode as long as the ECG indicates normal heart function. If the ECG indicates an abnormality, the sensing circuit 420 may cause the microprocessor to transition from the first mode to the second mode in order to deliver stimulation to the heart until the abnormality subsides. When the ECG again indicates normal heart function, the sensing circuit 420 may place the microprocessor 410 in the first mode in order to all the power supply circuit 405 to recharge its energy store. Of course, the example of an ECG and cardiac stimulation is not limiting on the present disclosure since the energy harvesting stimulators described herein may be used to monitor and stimulate any living tissue as would be appreciated by one of ordinary skill in the art.

Figure 5A:
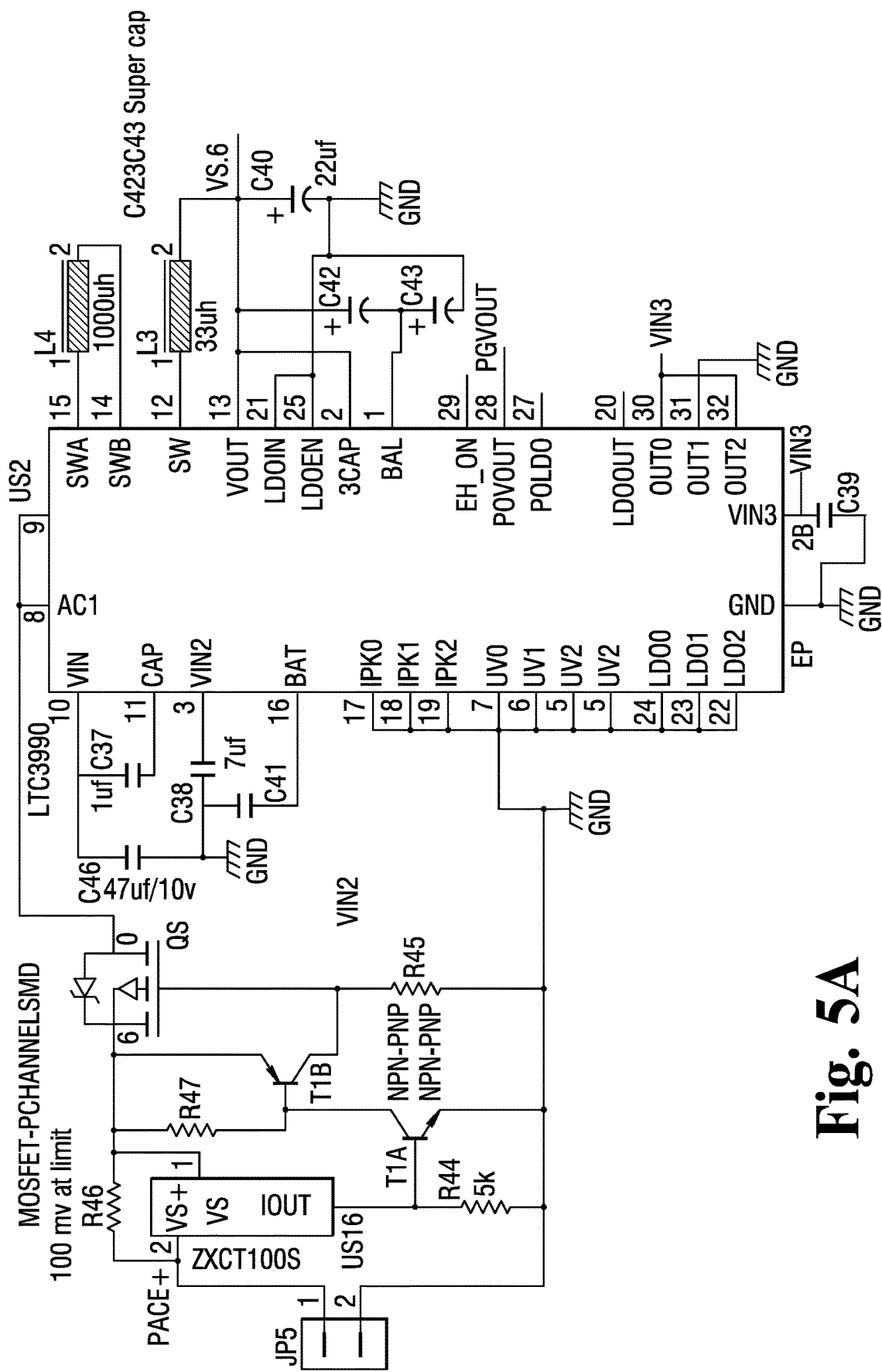
FIG. 5A is a first portion of a circuit diagram of the other energy harvesting stimulation device according to exemplary aspects of the present disclosure.
Figure 5B:
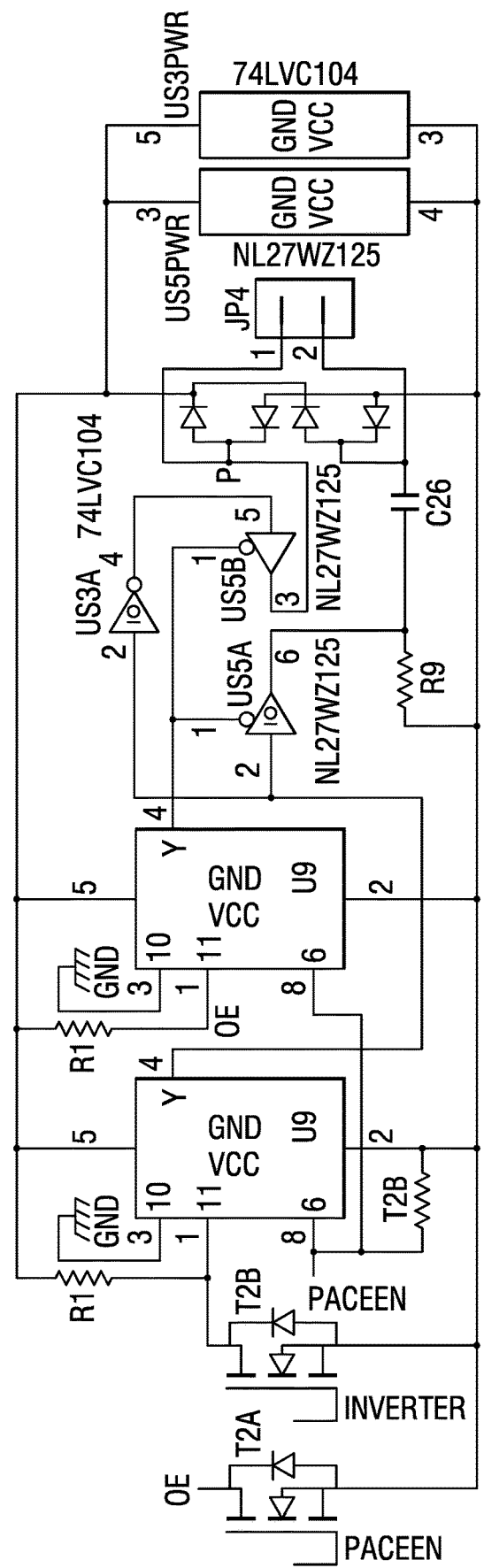
FIG. 5B is a second portion of the circuit diagram of the other energy harvesting stimulation device according to exemplary aspects of the present disclosure.

FIGS. 5A and 5B illustrate the circuitry of an energy harvesting stimulator that stores energy according to exemplary aspects of the present disclosure. In FIG. 5A, the energy from the output signal of the other stimulator 105 is received via the connector JP8 and is provided to a current regulator circuit formed by U16, T1A and T1B along with their associated passive components. The current source prevents excessive loading of the output of the other stimulator 105, and charges a capacitor C45 using the energy diverted from the output signal of the stimulator 105. The energy stored in the capacitor C45 is then used to by a micro-power switching regulator U$2, such as the LTC3330 from Linear Technologies, to generate a constant voltage. Optional capacitors C42 and C43 may be added to provide extra current during high-demand operations such as device programming via a radio telemetry link. As can be appreciated, the capacitors used in FIG. 5A should be selected to have the lowest leakage current possible to prevent wasted energy.

The switching regulator U$2 may optionally be provided with a battery B1 to power the circuit even if the stimulator 105 does not produce an output signal for an extended period of time, such as when the stimulator 105 is a demand pacemaker and the patient's heart is functioning normally. The battery B1 can be small since most of the driving energy is still derived from the energy diverted from the output leads of the stimulator 105. Essentially the small battery compensates for the leakage currents present when there is no energy to harvest.

The constant voltage generated by the switching regulator U$2 is used to power the microprocessor U4, which can be a PIC microcontroller from Microchip Corp. The microprocessor U4 performs the functions described above, and therefore will not be further described for the sake of brevity. FIG. 5A also includes a radio connector J2 to connect the energy harvesting stimulator to a radio for programming via telemetry as can be appreciated.

FIG. 5B includes the pulse generator circuit 415, which is formed by inverter U$3A, and tri state buffers U$5A and U$5B which perform the bridge function and can also serve to disconnect the patient side of the circuit when not in use. This circuit functions as described above with reference to the inverters of FIG. 3, but has the option to pass an unmodified signal from the input to the output, thereby allowing the stimulator to be bypassed. FIG. 5 also includes multiplexers U9 and U10 and transistors T2A and T2B which translate the very low voltage control signals of the microprocessor to the higher voltage of the pulse generator. The circuit of FIG. 5 also includes diodes between the pulse generator circuit formed by the inverters and the connector JP4 to protect the circuit from voltage and/or current spikes as described above with reference to FIG. 3. Also as described above with reference to FIG. 3, the stimulation signal generated by the pulse generator circuit is output to the living tissue via the connector JP4.

As can be appreciated, the circuits in FIGS. 5A-5B may be implemented using discrete components on a printed circuit board or may be implemented in an ASIC or other such custom integrated circuit device. Thus, the implementation illustrated in FIGS. 5A-5B is merely exemplary and should not be viewed as limiting upon the present disclosure.

Obviously, numerous modifications and variations of the present disclosure are possible in light of the above teachings. It is therefore to be understood that within the scope of the appended claims, the disclosure may be practiced otherwise than as specifically described herein.

The invention claimed is:

1. A stimulation device that stimulates living tissue, comprising:
   a power lead that physically connects to output leads of another device to receive energy from a first stimulation signal provided by the output leads of the other device to the living tissue;
   an energy harvesting circuit configured to receive the energy from the first stimulation output signal from the other device via the power lead and to power the stimulation device, immediately or otherwise, using the energy from the first stimulation output signal;
   a stimulation circuit configured to generate a second stimulation output signal to elicit a predetermined response from the living tissue; and
   at least one lead of the stimulation device configured to deliver the second stimulation output signal to the living tissue.

2. The stimulation device according to claim 1, wherein the stimulation circuit is further configured to generate the second stimulation output signal immediately upon receipt of the output signal by the energy harvesting circuit.

3. The stimulation device according to claim 2, wherein the living tissue stimulated by the stimulation device and the living tissue stimulated by the other device are different.

4. The stimulation device according to claim 2, wherein the living tissue stimulated by the stimulation device and the living tissue stimulated by the other device are the same.

5. The stimulation device according to claim 1, wherein the stimulation circuit includes a timer circuit configured to determine a pulse width of the second stimulation output signal, and a pulse generation circuit configured to generate the second stimulation output signal as at least one pulse with the pulse width determined by the timer circuit.

6. The stimulation device according to claim 5, wherein the second stimulation output signal includes at least a bi-phasic signal, a mono-phasic signal, a poly-phasic signal, an anodal signal, and a cathodal signal.

7. The stimulation device according to claim 1, wherein the energy harvesting circuit further includes
   a capacitor configured to store energy based on the first stimulation output signal received via the at least one power lead, and
   a power supply circuit configured to generate a predetermined voltage to power the stimulation circuit.

8. The stimulation device according to claim 7, wherein the stimulation circuit includes
   a microprocessor configured to determine waveform parameters of the second stimulation output signal, and
   a pulse generation circuit configured to generate the second stimulation output signal according to the waveform parameters determined by the microprocessor.

9. The stimulation device according to claim 8, wherein the waveform parameters include pulse width, pulse amplitude and a time interval between pulses.

10. The stimulation device according to claim 8, wherein the stimulation circuit is configured to function in a first mode in which the microprocessor is dormant and no stimulation signal is generated, and a second mode in which the microprocessor is active and the second stimulation output signal is generated.

11. The stimulation device according to claim 10, wherein the energy harvesting circuit continues to receive the first stimulation output signal and the capacitor continues to store energy from the first stimulation output signal when the stimulation circuit is functioning in the first mode.

12. The stimulation device according to claim 11, wherein the stimulation circuit is configured to transition from one of the first mode and the second mode to another of the first mode and the second mode at predetermined intervals.

13. The stimulation device according to claim 10, further comprising:
   a sensing circuit configured to sense at least one parameter via the at least one lead, and to cause the stimulation circuit to transition from one of the first and second modes to another of the first and second modes based on the at least one parameter.

14. The stimulation device according to claim 13, wherein the living tissue includes the heart, and the at least one parameter corresponds to an electrocardiograph waveform of the heart.

15. The stimulation device according to claim 13, wherein the living tissue includes the heart, and the at least one parameter corresponds to a beating rate of the heart.

16. The stimulation device according to claim 8, wherein the first stimulation output signal of the other device is configured to stimulate other living tissue, and the second stimulation output signal generated by the stimulation circuit is independent of the first stimulation output signal.

17. The stimulation device according to claim 1, wherein the stimulation device is configured to be implanted in a body corresponding to the living tissue.

18. The stimulation device according to claim 1, wherein the stimulation device is configured to remain outside of a body corresponding to the living tissue.

19. The stimulation device according to claim 1, wherein the other device is a pacemaker.

* * * * *